United States Patent
Mewshaw et al.

(10) Patent No.: US 6,245,780 B1
(45) Date of Patent: Jun. 12, 2001

(54) TETRAHYDROISOQUINOLINYL-INDOLE DERIVATIVES FOR THE TREATMENT OF DEPRESSION

(75) Inventors: Richard E. Mewshaw, King of Prussia, PA (US); Kristin L. Meagher, Hightstown, NJ (US)

(73) Assignee: American Home Products Corp, Madison, NJ (US)

( * ) Notice: Subject to any disclaimer, the term of this patent is extended or adjusted under 35 U.S.C. 154(b) by 0 days.

(21) Appl. No.: 09/551,137

(22) Filed: Apr. 17, 2000

Related U.S. Application Data

(60) Provisional application No. 60/155,207, filed on Apr. 22, 1999.

(51) Int. Cl.$^7$ .................................................. A01N 43/42
(52) U.S. Cl. .......................... 514/307; 514/309; 514/310; 546/141; 546/143; 546/148
(58) Field of Search .................... 514/307, 309, 514/310; 546/141, 143, 148

(56) References Cited

PUBLICATIONS

CA 130:237469, abstract of WO 9911619, Castro, Mar. 1999.*
CA 66:28694, abstract of Potts, J Heterocycl Chem, 1966, vol. 3(4), 395–401.*
CA 83:114705, abstract of Merlini, Gazz chim Ital, 1975, 105(3–4), 339–348.*
CA 89:197265, abstract of Solomina, Arm Khim Zh, 1978, 31(5), 345–348.*

* cited by examiner

Primary Examiner—D. Margaret Seaman
(74) Attorney, Agent, or Firm—Joseph M. Mazzarese

(57) ABSTRACT

Compounds are provided which have the formula:

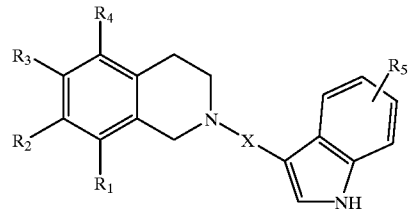

wherein:
  $R_1$, $R_2$, $R_3$, and $R_4$ are, independently, hydrogen, halogen, alkoxy, or carboxamide;
  $R_5$ is hydrogen, halogen, $CF_3$, CN, carbamide or alkoxy; and
  X is $(CH_2)_n$ or a 4–6 membered carbocyclic ring, wherein n is an integer of 2 to 4;
or pharmaceutically acceptable salts thereof.

17 Claims, No Drawings

TETRAHYDROISOQUINOLINYL-INDOLE DERIVATIVES FOR THE TREATMENT OF DEPRESSION

CROSS REFERENCE TO RELATED APPIICATIONS

This application claims the benefit of U.S. Provisional Application No. 60/155,207, which was converted from U.S. application Ser. No. 09/298,041, filed Apr. 22, 1999.

FIELD OF INVENTION

This invention relates to compounds which are useful for the treatment of diseases affected by disorders of the serotonin-affected neurological systems, such as depression and anxiety. More specifically, the present invention is directed to dihydroiosoquinolinyl-indole derivatives useful in the treatment of such disorders.

BACKGROUND OF INVENTION

Pharmaceuticals which enhance neurotransmission of serotonin (5-HT) are useful for the treatment of many psychiatric disorders, including depression and anxiety. The first generation of non-selective serotonin-affecting drugs operated through a variety of physiological functions which caused them to possess numerous undesired side-effects. The more recently prescribed drugs, the selective serotonin reuptake inhibitors (SSRIs), act predominately by inhibiting 5-HT, which is released at the synapses, from being actively removed from the synaptic cleft via a presynaptic serotonin transport carrier. Since SSRIs require several weeks before they exert their full therapeutic effect, this 5-HT blockade mechanism cannot fully account for their therapeutic activity. It is speculated that this two week induction, which occurs before a full antidepressant effect is observed, is due to the involvement of the 5HT1 A autoreceptors which suppress the firing activity of 5-HT neurons, causing a dampening of the therapeutic effect. Studies suggest that after several weeks of SSRI administration, a desensitization of the 5-HT autoreceptors occurs allowing a full antidepressant effect in most patients (see, e.g., LePaul et al., *Arch. Pharmacol.*, 352:141 (1995)). Hence, it is believed that overriding this negative feedback by using 5 HT1A antagonists would potentially increase and accelerate the clinical antidepressant response. Recent studies by Artigas et al., *Trends Neurosci.*, 19:378–383 (1996) suggested a combination of 5-HT1A activity and inhibition of 5-HT uptake within a single molecular entity can achieve a more robust and fast-acting antidepressant effect.

The present invention relates to a new class of molecules which have the ability to act at the 5-HT1A autoreceptors and concomitantly with the 5-HT transporter. Such compounds are therefore potentially useful for the treatment of depression as well as other serotonin disorders.

U.S. Pat. No. 5,468,767 discloses a series of substituted indoles of the following formula useful for the treatment of disorders associated with dysfunction in serotonergic neurotransmission, including depression.

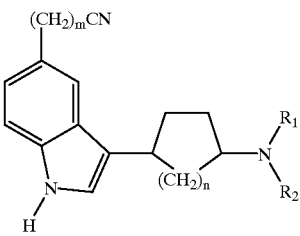

wherein:

$R_1$ is hydrogen or $C_{1-4}$ alkyl; and $R_2$ is $C_{1-4}$ alkyl or $(CH_2)_p Ar$.

WO 9415928 discloses reports a series of piperazine derivatives of the following formula for the treatment of CNS disorders, including depression.

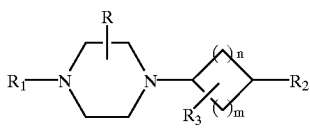

wherein:

R is hydrogen or alkyl, $R_1$ and $R_2$ are each mono or bicyclic aryl or heteroaryl radicals;

$R_3$ is hydrogen, alkyl, or a spirocycloalkyl group; and n is 1 or 2; and m is 1 or 3.

WO 93/10092 discloses a series of substituted cyclohexenes of the following formula for the treatment of dopaminergic disorders.

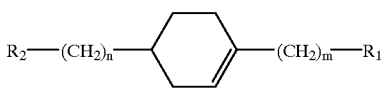

wherein:

$R_1$ is aryl; 2-, 3- or 4 pyridinyl; 2-, 4- or 5-pyrimidinyl; 2-pyrazinyl; 2- or 3-thienyl; 2- or 3-furanyl; or 2-, 4- or 5-thiazolyl;

m is zero or an integer from 1 to 2;

$R^2$ is

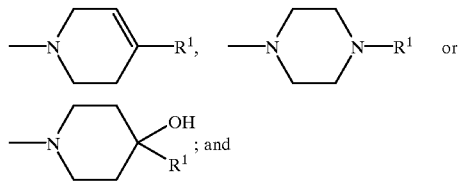

n is zero or an integer of 1 to 4.

SUMMARY OF THE INVENTION

The compounds of the present invention are dihydroisoquinolino-indole derivatives represented by Formula I:

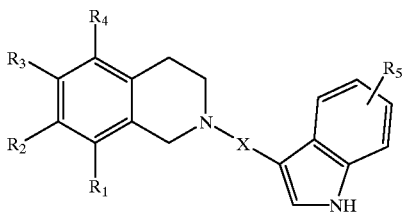

wherein:

$R_1$, $R_2$, $R_3$ and $R_4$ are, independently, hydrogen, halogen, alkoxy, or carboxamide;

$R_5$ is hydrogen, halogen, $CF_3$, CN, carbamide, or alkoxy; and

X is $(CH_2)_n$ or a 4–6-membered carbocyclic ring, wherein n is an integer of 2 to 4;

or pharmaceutically acceptable salts thereof.

DETAILED DESCRIPTION OF THE INVENTION

Preferably, the compounds of the present invention are those of Formula I, wherein:

$R_1$, $R_2$, $R_3$, and $R_4$ are, independently, hydrogen or alkoxy;

$R_5$ is halogen or CN; and

X is $(CH_2)_n$ or a 6-membered carbocyclic ring, wherein n is an integer of 2 to 3; or pharmaceutically acceptable salts thereof.

Most preferably, the compounds of the present invention are selected from:

3-[(1,4-cis)-4-(7-Methoxy-3,4-dihydro-1H-isoquinolin-2-yl)-cyclohexyl]-1H-indole-5-carbonitrile;

3-[(1,4-trans)-4-(7-Methoxy-3,4-dihydro-1H-isoquinolin-2-yl)-cyclohexyl]-1H-indole-5-carbonitrile;

3-[(1,4-cis)-4-(8-Methoxy-3,4-dihydro-1H-isoquinolin-2-yl)-cyclohexyl]-1H-indole-5-carbonitrile;

3-[(1,4-trans)-4-(8-Methoxy-3,4-dihydro-1H-isoquinolin-2-yl)-cyclohexyl]-1H-indole-5-carbonitrile;

3-[(1,4-cis)-4-(6-Methoxy-3,4-dihydro-1H-isoquinolin-2-yl)-cyclohexyl]-1H-indole-5-carbonitrile;

3-[(1,4-trans)-4-(6-Methoxy-3,4-dihydro-1H-isoquinolin-2-yl)cyclohexyl]-1H-indole-5-carbonitrile;

3-[(1,4-cis)-4-(5-Methoxy-3,4-dihydro-1H-isoquinolin-2-yl)-cyclohexyl]-1H-indole-5-carbonitrile;

3-[(1,4-trans)-4-(5-Methoxy-3,4-dihydro-1H-isoquinolin-2-yl)-cyclohexyl]-1H-indole-5-carbonitrile;

3-[(1,4-cis)-4-(3,4-Dihydro-1H-isoquinolin-2-yl)-cyclohexyl]-1H-indole-carbonitrile;

3-[(1,4-trans)-4-(3,4-Dihydro-1H-isoquinolin-2-yl)-cyclohexyl]-1H-indole-carbonitrile;

2-[3-(5-Fluoro-1H-indol-3-yl)-propyl]-5-methoxy-1,2,3,4-tetrahydroisoquinoline;

2-[3-(5-Fluoro-1H-indol-3-yl)-propyl]-6-methoxy-1,2,3,4-tetrahydroisoquinoline; and 2-[3-(5-Fluoro-1H-indol-3-yl)-propyl]-1,2,3,4-tetrahydroisoquinoline;

As used here, the term "alkoxy" is meant to include both straight and branched carbon atoms. The term "halogen" is meant to include fluorine, chlorine, bromine and iodine.

The compounds of Formula I also may be used in the form of a pharmaceutically acceptable acid addition salt having the utility of the free base. Such salts, prepared by methods well known to the art are formed with both inorganic or organic acids, for example: fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzenesulfonic, hydrochloric hydrobromic, sulfuric, cyclohexylsulfamic, phosphoric and nitric acids.

The compounds of the present invention may be prepared by any suitable method which will be recognized by those skilled in the art. However, the present compounds may be advantageously prepared according to Scheme I below.

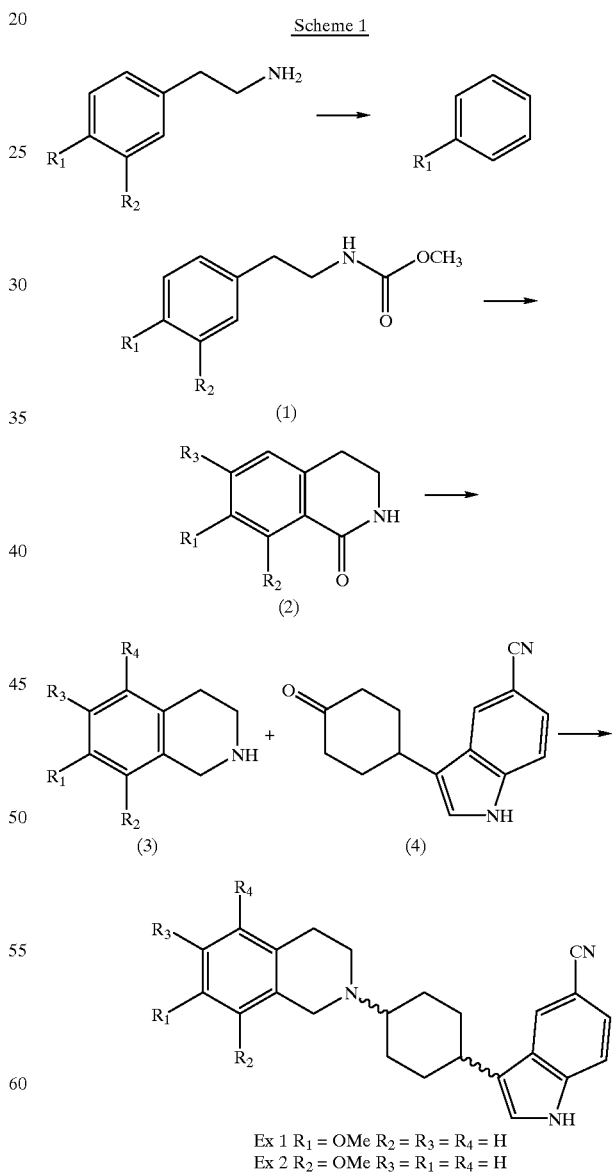

Ex 1 $R_1$ = OMe $R_2$ = $R_3$ = $R_4$ = H
Ex 2 $R_2$ = OMe $R_3$ = $R_1$ = $R_4$ = H
Ex 3 $R_3$ = OMe $R_1$ = $R_2$ = $R_4$ = H
Ex 4 $R_4$ = OMe $R_1$ = $R_2$ = $R_3$ = H
Ex 5 $R_1$ = $R_2$ = $R_3$ = $R_4$ = H

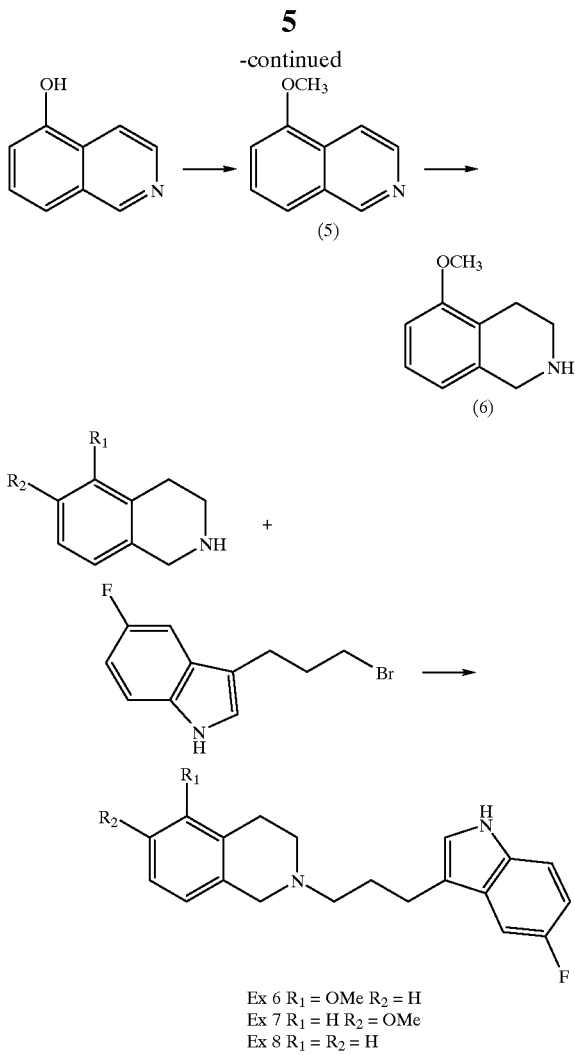

Ex 6 R₁ = OMe R₂ = H
Ex 7 R₁ = H R₂ = OMe
Ex 8 R₁ = R₂ = H

Specific exemplification of the preparation of representative compounds of this invention is provided in the following procedures.

INTERMEDIATE 1a

N-(Methoxycarbonyl)-2-(4-methoxyphenyl)ethylamine

To a solution of 4-methoxy-phenethylamine (5.81 mL, 39.7 mmol) in anhydrous THF (200 mL) was added Et$_3$N (6.6 mL, 48 mmol). The solution was cooled to 0° C. and methyl chloroformate (15.38 mL, 199 mmol) was added slowly via syringe. The reaction was stirred at 0° C. for 2 hours and then allowed to warm to room temperature and stirred overnight. To the reaction mixture was added H$_2$O (50 mL) and the resulting solution was extracted into Et$_2$O (1×100 mL) and then into EtOAc (2×75 mL). The combined organic fractions were washed with brine (200 mL) and 1 M HCl (200 mL), dried over Na$_2$SO$_4$, filtered and concentrated under vacuum, affording 7.98 g (96%) of the title compound as a pale yellow solid.

INTERMEDIATE 1b

N-(Methoxycarbonyl)-2-(3-methoxyphenyl)ethylamine

This compound was prepared in the manner described for Intermediate 1a, replacing 4-methoxy-phenethylamine with 3-methoxy-phenethylamine (10 g, 66 mmol) affording 13.6 g (98%) of the title compound as a gold oil.

INTERMEDIATE 2a 7-Methoxy-3,4-dihydro-2H-isoquinolin-1-one

To a stirred solution of polyphosphoric acid (50 g) at 145° C. was added N-(methoxycarbonyl)-2-(4-methoxyphenyl)ethylam (4.5 g, 21.5 mmol). The resulting brown solution was stirred at 140° C. for 40 min. The hot reaction mixture was poured onto ice, and extracted in CH$_2$Cl$_2$ (3×200 mL). The organic fractions were combined, dried over Na$_2$SO$_4$, filtered, and concentrated. The crude oil was purified by column chromatography with 10% MeOH/CH$_2$Cl$_2$ as the eluent, affording 1.11 g (30%) of the title compound as a pale yellow solid: mp 90–93° C.

Elemental Analysis for C$_{10}$H$_{11}$NO$_2$: Calc'd: C, 67.78; H, 6.26; N, 7.90; Found: C, 67.88; H, 6.54; N, 7.90.

INTERMEDIATE 2b

6-Methoxy-3,4-dihydro-2H-isoquinolin-1-one

This compound was prepared in the same manner as Intermediate 2a, replacing N-(methoxycarbonyl)-2-(4-methoxyphenyl)ethylamine with N-(methoxycarbonyl)-2-(3 methoxyphenyl)ethylamine (6 g, 28.7 mmol) affording 2.42 g (48%) of the title compound as a white solid: mp 131–133° C.

Elemental Analysis for C$_{10}$H$_{11}$NO$_2$; Calc'd: C, 67.78; H, 6.26; N, 7.90; Found: C, 67.55; H, 6.36; N, 7.86.

INTERMEDIATE 2c

8-Methoxy-3,4-dihydro-2H-isoquinolin-1-one

This compound was isolated at the same time as Intermediate 2b, affording 0.67 g (13%) as a white solid: mp 140–142° C.

Elemental Analysis for C$_{10}$H$_{11}$NO$_2$.0.1H$_2$O; Calc'd: C, 67.10; H, 6.31; N, 7.82; Found: C, 66.92; H, 6.49; N, 7.70.

INTERMEDIATE 3a

7-Methoxy-1,2,3,4-tetrahydro-isoquinoline

A solution of Intermediate 2a (1 g, 5.6 mmol) dissolved in anhydrous THF (30 mL) was dripped slowly into a LAH solution (7.35 mL, 1 M in THF) at 0° C. under a N$_2$ atmosphere. The resulting solution was heated at reflux for 2 hours. The reaction mixture was cooled to 0° C. and H$_2$O was added dropwise to quench. The resulting solution was basified with 1 M NaOH (100 mL), filtered through a bed of celite, and extracted into EtOAc (3×150 mL). The organic fractions were combined, dried over Na$_2$SO$_4$, filtered and concentrated yielding 0.88 g (96%) of a pale yellow oil. The HCl salt was made in EtOAc affording a white solid: mp 224–227° C.

Elemental Analysis for C$_{10}$H$_{13}$N.HCl; Calc'd: C, 60.15; H, 7.07; N, 7.01; Found: C, 60.11; H, 7.12; N, 6.87.

INTERMEDIATE 3b

6-Methoxy-1,2,3,4-tetrahydro-isoquinoline

This compound was prepared in the same manner as Intermediate 3a by replacing Intermediate 2a with Intermediate 2b (1 g, 5.6 mmol) affording 0.87 g (95%) of the title compound as a pale yellow oil. The HCl salt was made in EtOAc affording a white solid: mp 236–238° C.

Elemental Analysis for $C_{10}H_{13}N.HCl$; Calc'd: C, 60.15; H, 7.07; N, 7.01; Found: C, 60.12; H, 6.99; N, 6.82.

INTERMEDIATE 3c

8-Methoxy-1,2,3,4-tetrahydro-isoquinoline

This compound was prepared in the same manner as Intermediate 3a by replacing Intermediate 2a with Intermediate 2c (0.600 g, 3.4 mmol) alfording 0.41 g (74%) of the title compound as a pale yellow oil. The HCl salt was made in EtOAc affording a white solid: mp dec>210° C.

Elemental Analysis for $C_{10}H_{13}N.HCl$; Calc'd: C, 60.15; H, 7.07; N, 7.01; Found: C, 59.98; H, 6.97; N, 6.83.

INTERMEDIATE 5

5-Methoxy-isoquinoline

To an oven dry three neck flask was added 5-hydroxyquinoline (5 g, 34.5 mmol), and triphenylphosphine. The solids were dissolved in THF (100 mL) and DEAD (8.19 mL, 51.7 mmol) was added slowly. The maroon reaction mixture was stirred at room temperature overnight and then poured into $H_2O$ (100 mL) and extracted into EtOAc (3×150 mL). The combined organic fractions were dried over $Na_2SO_4$, filtered, concentrated, and purified by column chromatography using 20% EtOAc/hexanes as the eluent. The title compound was isolated as 3.5 g (64%) of a white solid.

INTERMEDIATE 6

5-Methoxy-1,2,3,4-tetrahydro-isoquinoline

To a Parr hydrogenation flaslk was added $PtO_2$ (165 mg) and the solid was purged with $N_2$ for 10 minutes. A solution of 5-methoxy-isoquinoline in HOAc (40 mL) was added to the flask and hydrogenated at 40 psi overnight. The resulting solution was filtered through celite, concentrated and basified with 1 M NaOH (100 mL) and extracted into EtOAc (3×150 mL). The organic fractions were combined, dried over $Na_2SO_4$, filtered, concentrated and purified by column chromatography with 10% $MeOH/CH_2CH_2/NH_4OH$ as the eluent. The title compound was obtained as 2.49 g (70%) of a white solid: mp 124–126; MS EI m/e 163 $M^+$.

EXAMPLE 1a

3-[(1,4-cis)-4-(7-Methoxy-3,4-dihydro-1H-isoquinolin-2-yl)-cyclohexyl]-1H-indole-5-carbonitrile To a solution of 7-methoxy-1,2,3,4-tetrahydro-isoquinoline (500 mg, 3.1 mmol), 4-(5-cyano-1H-3-indolyl)-cyclohexanone (730 mg, 3.1 mmol), and sodium triacetoxyborohydride (975 mg, 4.6 mmol) in dichloroethane (50 mL) was added acetic acid (0.35 mL, 6.1 mmol) and the mixture was stirred overnight at room temperature. The reaction was quenched with 1 M NaOH (100 mL) and extracted in $CH_2Cl_2$ (3×100 mL) and EtOAc (2×100 mL). The organic fractions were combined, dried over $Na_2SO_4$, concentrated, filtered and chromatographed (5% MeOH/EtOAc) yielding 480 mg (40%) of the cis isomer as a gold oil. The HCl salt was generated from EtOAc yielding a pale yellow solid: mp dec>145° C.

Elemental Analysis for $C_{25}H_{27}N_3O.HCl.0.25H_2O$; Calc'd: C, 70.41; H, 6.74; N, 9.85; Found: C, 69.91; H, 6.69; N, 9.75.

EXAMPLE 1b

3-[(1,4-trans)-4-(7-Methoxy-3,4-dihydro-1H-isoquinolin-2-yl)-cyclohexyl]-1H-indole-5-carbonitrile The trans isomer was isolated at the same time as Example 1a, affording 320 mg (27%) as a pale yellow solid: mp dec>140° C.

Elemental Analysis for $C_{25}H_{27}N_3O.0.25H_2O$; Calc'd: C, 76.99; H, 7.11; N, 10.77; Found: C, 76.79; H, 7.09; N, 10.50.

EXAMPLE 2a

3-[(1,4-cis)-4-(8-Methoxy-3,4-dihydro-1H-isoquinolin-2-yl)-cyclohexyl]-1H-indole-5-carbonitrile This compound was prepared in the same manner as Example 1a replacing 7-methoxy-1,2,3,4-tetrahydro-isoquinoline with 8-methoxy-1,2,3,4-tetrahydro-isoquinoline (300 mg, 1.85 mmol) to afford 300 mg (44%) of the title compound as a yellow oil. The HCl salt was prepared from EtOAc yielding a white solid: mp dec>155° C.

Elemental Analysis for $C_{25}H_{27}N_3O.HCl.0.50H_2O$; Calc'd: C, 69.67; H, 6.78; N, 9.75; Found: C, 69.91; H, 6.77; N, 9.89.

EXAMPLE 2b

3-[(1,4-trans)-4-(8-Methoxy-3,4-dihydro-1H-isoquinolin-2-yl)-cyclohexyl]-1H-indole-5-carbonitrile The trans isomer was isolated at the same time as the cis isomer of Example 2a, affording 200 mg (28%) as a pale yellow solid. The HCl salt was generated from EtOAc affording a white solid: mp dec>250° C.

Elemental Analysis for $C_{25}H_{27}N_3O.HCl.0.25H_2O$; Calc'd: C, 70.41; H, 6.74; N, 9.85; Found: C, 70.48; H, 6.65; N, 9.69.

EXAMPLE 3a 3-[(1,4-cis)-4-(6-Methoxy-3,4-dihydro-1H-isoquinolin-2-yl)-cyclohexyl]-1H-indole-5-carbonitrile This compound was prepared in the same manner as Example 1a, replacing 7-methoxy-1,2,3,4-tetrahydro-isoquinoline with 6-methoxy-1,2,3,4-tetrahydro-isoquinoline (500 mg, 3.1 mmol) to afford 520 mg (44%) of the title compound as a yellow oil. The HCl salt was prepared from EtOAc yielding a white solid: mp dec>180° C.

Elemental Analysis for $C_{25}H_{27}N_3O.HCl.0.25H_2O$; Calc'd: C, 70.41; H, 6.74; N, 9.85; Found: C, 70.21; H, 6.80; N, 9.63.

EXAMPLE 3b

3-[(1,4-trans)-4-(6-Methoxy-3,4-dihydro-1H-isoquinolin-2-yl)-cyclohexyl]-1H-indole-5-carbonitrile The trans isomer was isolated at the same time as the cis isomer of Example 3a, affording 250 mg (21%) as a pale yellow solid: mp dec>200° C.

Elemental Analysis for $C_{25}H_{27}N_3O.0.25H_2O$; Calc'd: C, 76.99; H, 7.11; N, 10.77; Found: C, 76.81; H, 7.08; N, 10.56.

EXAMPLE 4a

3-[(1,4-cis)-4-(5-Methoxy-3,4-dihydro-1H-isoquinolin-2-yl)-cyclohexyl]-1H-indole-5-carbonitrile This compound was prepared in the same manner as Example 1a, replacing 7-methoxy-1,2,3,4-tetrahydro-isoquinoline with 5-methoxy-1,2,3,4-tetrahydro-isoquinoline (500 mg, 3.1 mmol) to afford 400 mg (34%) of the title compound as a pale yellow solid: mp 223–226° C.

Elemental Analysis for $C_{25}H_{27}N_3O \cdot 0.85H_2O$; Calc'd: C, 74.91; H, 7.22; N, 10.48; Found: C, 75.30; H, 7.15; N, 10.08.

EXAMPLE 4b

3-[(1,4-trans)-4-(5-Methoxy-3,4-dihydro-1H-isoquinolin-2-yl)-cyclohexyl]-1H-indole-5-carbonitrile The trans isomer was isolated at the same time as the cis isomer of Example 4a affording 200 mg (17%) as a white solid. The HCl salt was generated in EtOAc yielding a white solid: mp dec>181° C.

Elemental Analysis for $C_{25}H_{27}N_3O \cdot HCl \cdot 1H_2O$; Calc'd: C, 68.25; H, 6.87; N, 9.55; Found: C, 68.23; H, 6.64; N, 9.33.

EXAMPLE 5a

3-[(1,4-cis)-4-(3,4-Dihydro-1H-isoquinolin-2-yl)-cyclohexyl]-1H-indole-5-carbonitrile This compound was prepared in the same manner as Example 1a replacing 7-methoxy-1,2,3,4-tetrahydro-isoquinoline with commercially available 1,2,3,4-tetrahydro-isoquinoline (250 mg, 2.1 mmol) to afford 330 mg (44%) of the title compound as a yellow solid. The HCl salt was generated from EtOAc yielding an off white solid: mp 188–191° C.

Elemental Analysis for $C_{24}H_{25}N_3 \cdot HCl \cdot 0.75H_2O$; Calc'd: C, 71.10; H, 6.84; N, 10.36; Found: C, 71.37; H, 6.82; N, 9.89.

EXAMPLE 5b

3-[(1,4-trans)-4-(3,4-Dihydro-1H-isoquinolin-2-yl)-cyclohexyl]-1H-indole-carbonitrile The trans isomer was isolated at the same time as the cis isomer of Example 5a affording 250 mg (21%) as a pale yellow solid: mp 196–200° C.

Elemental Analysis for $C_{24}H_{25}N_3 \cdot 0.25H_2O$; Calc'd: C, 80.08; H, 7.14; N, 11.67; Found: C, 80.01; H, 7.14; N, 11.37.

EXAMPLE 6

2-[3-(5-Fluoro-1H-indol-3-yl)-propyl]-5-methoxy-1,2,3,4-tetrahydroisoquinoline A solution of 5-methoxy-1,2,3,4-tetrahydro-isoquinoline (500 mg, 3.1 mmol), 3-(5-fluoro-indolyl)-propylbromide (604 mg, 2.36 mmol) and $Et_3N$ (0.86 mL, 6.2 mmol) was dissolved in DMSO (20 mL) and heated at 100° C. for 5 hours then at room temperature overnight. The reaction was poured into $H_2O$ (150 mL) and extracted into EtOAc (2×100 mL). The organic fractions were combined and washed with $NaHCO_3$ (150 mL), dried over $Na_2SO_4$, filtered, and concentrated. The resulting oil was purified by column chromatography using 5% MeOH/EtOAc as the eluent yielding 570 mg (71%) of a gold oil. The HCl salt was generated from EtOAc affording a white solid: mp 183–186° C.

Elemental Analysis for $C_{21}H_{23}FN_2O \cdot HCl$; Calc'd: C, 67.28; H, 6.45; N, 7.47; Found: C, 67.00; H, 6.52; N, 7.30.

EXAMPLE 7

2-[3-(5-Fluoro-1H-indol-3-yl)-propyl]-6-methoxy-1,2,3,4-tetrahydroisoquinoline This compound was prepared in the same manner as Example 6, replacing 5-methoxy-1,2,3,4-tetrahydro-isoquinoline with 6-methoxy-1,2,3,4-tetrahydroisoquinoline (190 mg, 1.16 mmol) affording the title compound as a brown oil. The HCl salt was generated from EtOAc yielding a hygroscopic tan solid: mp dec>90° C.

Elemental Analysis for $C_{21}H_{23}FN_2O \cdot HCl \cdot H_2O$; Calc'd: C, 64.20; H, 6.67; N, 7.13; Found: C, 64.18; H, 6.51; N, 6.90.

EXAMPLE 8

2-[3-(5-Fluoro-1H-indol-3-yl)-propyl]-1,2,3,4-tertrahydroisoquinoline

This compound was prepared in the same manner as Example 6, replacing 5-methoxy-1,2,3,4-tetrahydro-isoquinoline with commercial 1,2,3,4-tetralhydro-isoquinoline (500 mg, 4.2 mmol) affording 730 mg as a waxy orange solid. The HCl salt was generated from EtOAc yielding a pale yellow solid: mp 235–238° C.

Elemental Analysis for $C_{20}H_{21}FN_2 \cdot HCl$; Calc'd: C, 69.66; H, 6.43; N, 8.12; Found: C, 69.55; H, 6.34; N, 7.84.

The activity of the present compounds is demonstrated by the following standard pharmacological test procedures.

The PCR cloning of the human $5\text{-}HT_{1A}$ receptor subtype from a human genomic library has been described previously by Chanda et al., *Mol. Pharmacol.*, 43:516 (1993). A stable Chinese hamster ovary cell line expressing the human $5\text{-}HT_{1A}$ receptor subtype ($5\text{-}HT_{1A}$.CHO cells) was employed throughout this study. Cells were maintained in DMEM supplemented with 10% fetal calf serum, non-essential amino acids and penicillin/streptomycin.

Cells were grown to 95–100% confluency as a monolayer before membranes were harvested for binding studies. Cells were gently scraped from the culture plates, transferred to centrifuge tubes, and washed twice by centrifugation (2000 rpm for 10 min., 4° C.) in buffer (50 mM Tris; pH 7.5). The resulting pellets were aliquoted and maintained at −80° C. On the day of assay, the cells were thawed on ice, and resuspended in buffer. Studies were conducted using [$^3$H]8-OH-DPAT as the radioligand. The binding assay was performed in 96 well microtiter plates in a final total volume of 250 µL of buffer. Comparison experiments were performed by using 7 concentrations of unlabelled drug and a final ligand concentration of 1.5 nM. Non-specific binding was determined in the presence of 10 µM 5HT. Saturation analysis was conducted by using [$^3$H]8-OH-DPAT at concentrations ranging from 0.3–30 nM. Following a 30 minute incubation at room temperature, the reaction was terminated by the addition of ice cold buffer and rapid filtration using a M-96 Brandel Cell Harvester (Gaithersburg, Md.) through a GF/B filter presoaked for 30 minutes in 0.5% polyethyleneimine.

A protocol similar to that used by Cheetham et al., *Neuropharmacol.*, 32:737 (1993) was used to determine the affinity of compounds for the serotonin transporter. Briefly, frontal cortical membranes prepared from male Sprague-Dawley rats were incubated with $^3$H-parsoxetine (0.1 nM) for 60 min at 25° C. All tubes also contained either vehicle, test compound (one to eight concentrations), or a saturating concentration of fluoxetine (10 $\mu$M) to define specific binding. All reactions were terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Nonlinear regression analysis was used to determine IC$_{50}$ values which were converted to Ki values using the method set forth in Cheng and Prusoff, *Biochem. Pharmacol.*, 22:3099 (1973) (Ki=IC50/((Radioligand conc.)/(1+KD)).

The [$^{35}$S]-GTP$\gamma$S binding assay was similar to that used by Lazareno and Birdsall, *Br. J. Pharmacol.* 109:1120 (1993). Briefly, 5-HT$_{1A}$ cloned receptor membrane fragments (as used for 5-HT$_{1A}$ receptor binding assays) were stored at −70° C. When needed, membranes were rapidly thawed, centrifuged at 40,000×g for 10 minutes and resuspended at 4° C. for 10 minutes in assay buffer (25 mM HEPES, 3 mM MgCl$_2$, 100 mM NaCl, 1 mM EDTA, 10 uM GDP, 500 mM DTT, pH 8.0). These membranes were then incubated for 30 min at 30° C. with [$^{35}$S]GTPgS (1 nM) in the presence of vehicle, test compound (one to eight concentrations), or excess 8-OH-DPAT to define maximum agronist response. All reactions were terminated by the addition of ice cold Tris buffer followed by rapid filtration using a Tom Tech® filtration device to separate bound from free [$^{35}$S]GTPgS. Agonists produced an increase in the amount of [$^{35}$S]GTPgS bound whereas antagonists produced no increase in binding. Bound radioactivity was counted and analyzed as above.

The following assays were performed by incubating the cells with DMEM containing 25 mM HEPES, 5 mM theophylline and 10 $\mu$M pargyline for a period of 20 minutes at 37° C. Functional activity was assessed by treating the cells with forskolin (1 uM final concentration) followed immediately by test Compound (6 concentrations) for an additional 10 min at 37° C. In separate experiments, 6 concentrations of antagonist were preincubated for 20 min prior to the addition of 10 nM 8-OH-DPAT and forskolin. The reaction was terminated by removal of the media and addition of 0.5 ml ice cold assay buffer. Plates were stored at −20° C. prior to assessment of cAMP formation by a cAMP SPA assay (Amersham).

TABLE A

| Example No. | 5-HT$_{1A}$ [Ki, nM: (% inh @ 1 uM)] | ST (K$_i$, nM,) | GTPgS ED50 (% EMax) |
|---|---|---|---|
| 1a | (26%) | 0.8 | |
| 1b | (48%) | 12 | |
| 2a | (14%) | 1.0 | |
| 2b | (46%) | 7.5 | |
| 3a | (21%) | 0.1 | |
| 3b | 300 | 8.0 | (0%) |
| 4a | (7%) | 0.61 | (12%) |
| 4b | (47%) | 12.0 | 350 (33%) |
| 5a | (0%) | 1.3 | |
| 5b | (10%) | 10.0 | |
| 6 | 243 | 1.9 | 1346 (23%) |
| 7 | 288 | 1.4 | (100%) |
| 8 | (48%) | 4.85 | (13%) |

As demonstrated by the results set forth above, the compounds of the present invention are active towards 5HT1A receptors and generally elevate serotonin levels by inhibiting 5-HT transport: Accordingly, the present compounds should be useful in treating disorders related to defects in serotonin concentration.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Any of the solid carriers known to those skilled in the art may be used with the compounds of this invention. Particularly suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and ion exchange resins.

Liquid carriers may be used in preparing solutions, suspensions, emulsions, syrups and elixirs of the compounds of this invention. The compounds of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) and their derivatives and oils (e.g., fractionated coconut oil and arachis oil). For parenteral administration, the carrier can also be an oily ester such as ethyl oleate and isopropyl myristate. Sterile liquid carriers are used in compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Compositions for oral administration may be either liquid or solid composition form.

Preferably, the pharmaceutical compositions containing the compounds of this invention are in unit dosage form, e.g., tablets or capsules. In such form, the compositions may be sub-divided in unit doses containing appropriate quantities of the present compounds. The unit dosage forms can be packaged compositions, for example, packeted powders, vials, ampoules, prefilled syringes or sachets containing liquids. Alternatively, the unit dosage form can be, for example, a capsule or tablet itself, or it can be the appropriate number of any such compositions in package form.

The therapeutically effective amount of the compounds of this invention that is administered and the dosage regimen depends on a variety of factors, including the weight, age, sex, and medical condition of the subject, the severity of the disease, the route and frequency of administration, and the specific compound employed, and thus may vary widely. However, it is believed that the pharmaceutical compositions may contain the compounds of this invention in the range of about 0.1 to about 2000 mg, preferably in the range of about 0.5 to about 500 mg and more preferably between about 1 and about 100 mg. Projected daily dosages of active compound are about 0.01 to about 100 mg/kg body weight. The daily dose can be conveniently administered two to four times per day.

The present invention may be embodied in other specific forms without departing from the spirit and essential attributes thereof and accordingly, reference should be made to the appended claims, rather than to the foregoing specification, as indicating the scope of the invention.

What is claimed is:

1. A compound of the formula:

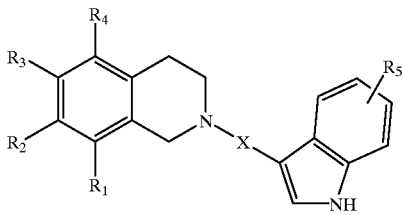

wherein:
$R_1$, $R_2$, $R_3$, and $R_4$ are, independently, hydrioen, halogen, alkoxy, or carboxamide;
$R_5$ is halogen, $CF_3$, CN, carbamide or alkoxy; and
X is $(CH_2)_n$ or a 4–6-membered carbocyclic ring, wherein n is an integer of 2 to 4;
or pharmaceutically acceptable salts thereof.

2. A compound as in claim 1, wherein
$R_1$, $R_2$, $R_3$, and $R_4$ are, independently, hydrogen or alkoxy;
$R_5$ is halogen or CN; and
X is $(CH_2)_n$ or a 6-membered carbocyclic ring, wherein n is an integer of 2 to 3; or
pharmaceutically acceptable salts thereof.

3. A compound as in claim 1 which is 3-[(1,4-cis)-4-(7-Methoxy-3,4-dihydro-1H-isoquinolin-2-yl)-cyclohexyl]-1H-indole-5-carbonitrile.

4. A compound as in claim 1 which is 3-[(1,4-trans)-4-(7-Methoxy-3,4-dihydro-1H-isoquinolin-2-yl)-cyclohexyl]-1H-indole-5-carbonitrile.

5. A compound as in claim 1 which is 3-[(1,4-cis)-4-(8-Methoxy-3,4-dihydro-1H-isoquinolin-2-yl)-cyclohexyl]-1H-indole-5-carbonitrilc.

6. A compound as in claim 1 which is 3-[(1,4-trans)-4-(8-Methoxy-3,4-dihydro-1H-isoquinolin-2-yl)-cyclohexyl]-1H-indole-5-carbonitrile.

7. A compound as in claim 1 which is 3-[(1,4-cis)-4-(6-Methoxy-3,4-dihydro-1H-isoquinolin-2-yl)-cyclohexyl]-1H-indole-5-carbonitrile.

8. A compound as in claim 1 which is 3-[(1,4-trans)-4-(6-Methoxy-3,4-dihydro-1H-isoquinolin-2-yl)cyclohexyl]-1H-indole-5-carbonitrile.

9. A compound as in claim 1 which is 3-[(1,4-cis)-4-(5-Methoxy-3,4-dihydro-1H-isoquinolin-2-yl)-cyclohexyl]-1H-indole-5-carbonitrile.

10. A compound as in claim 1 which is 3-[(1,4-trans)-4-(5-Methoxy-3,4-dihydro-1H-isoquinolin-2-yl)-cyclohexyl]-1H-indole-5-carbonitride.

11. A compound as in claim 1 which is 3-[(1,4-cis)-4-(3,4-Dihydro-1H-isoquinolin-2-yl)-cyclohexyl]-1H-indole-carbonitrile.

12. A compound as in claim 1 which is 3-[(1,4-trans)-4-(3,4-Dihydro-1H-isoquinolin-2-yl)-cyclohexyl]-1H-indole-carbonitrile.

13. A compound as in claim 1 which is 2-[3-(5-Fluoro-1H-indol-3-yl)propyl]-5-methoxy-1,2,3,4-tetrahydroisoquinoline.

14. A compound as in claim 1 which is 2-[3-(5-Fluoro-1H-indol-3-yl)propyl]-6-methoxy-1,2,3,4-tetrahydroisoquinoline.

15. A compound as in claim 1 which is 2-[3-(5-Fluoro-1H-indol-3-yl)propyl]-1,2,3,4-tetrahydroisoquinoline.

16. A pharmaceutical composition comprising a compound of the formula:

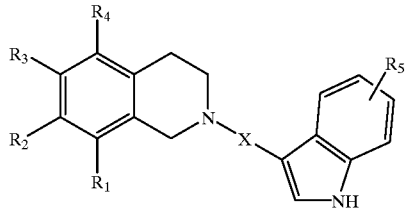

wherein:
$R_1$, $R_2$, $R_3$, and $R_4$ are, independently, hydrogen, halogen, alkoxy, or carboxamide;
$R_5$ is halogen, $CF_3$, CN, carbamide or alkoxy; and
X is $(CH_2)_n$ or a 4–6 membered carbocyclic ring, wherein n is an integer of 2 to 4;
or pharmaceutically acceptable salts thereof.

17. A method of treating depression in a patient in need thereof, comprising administering to said patient an antidepressant effective amount of a compound of the formula:

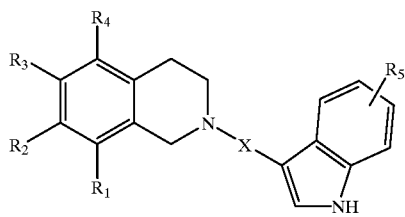

wherein:
$R_1$, $R_2$, $R_3$, and $R_4$ are, independently, hydrogen, halogen, alkoxy, or carboxamide;
$R_5$ is halogen, $CF_3$, CN, carbamide or alkoxy; and
X is $(CH_2)_n$ or a 4–6 membered carbocyclic ring, wherein n is an integer of 2 to 4;
or pharmaceutically acceptable salts thereof.

* * * * *